US009788759B2

(12) United States Patent
Ferrantelli

(10) Patent No.: US 9,788,759 B2
(45) Date of Patent: Oct. 17, 2017

(54) METHOD AND SYSTEM FOR POSTURAL ANALYSIS AND MEASURING ANATOMICAL DIMENSIONS FROM A DIGITAL THREE-DIMENSIONAL IMAGE ON A MOBILE DEVICE

(71) Applicant: Joseph Ralph Ferrantelli, Trinity, FL (US)

(72) Inventor: Joseph Ralph Ferrantelli, Trinity, FL (US)

(*) Notice: Subject to any disclaimer, the term of this patent is extended or adjusted under 35 U.S.C. 154(b) by 128 days.

(21) Appl. No.: 14/598,937

(22) Filed: Jan. 16, 2015

(65) Prior Publication Data
US 2015/0223730 A1 Aug. 13, 2015

Related U.S. Application Data

(63) Continuation-in-part of application No. 14/037,526, filed on Sep. 26, 2013, which is a continuation-in-part
(Continued)

(51) Int. Cl.
*A61B 6/00* (2006.01)
*A61B 5/107* (2006.01)
(Continued)

(52) U.S. Cl.
CPC .......... *A61B 5/1079* (2013.01); *A61B 5/0077* (2013.01); *A61B 5/1072* (2013.01);
(Continued)

(58) Field of Classification Search
CPC ....... A61B 5/6853; A61B 5/72; A61B 5/7425;
A61B 5/0086; A61B 8/4477; A61B 1/00181; A61B 8/4444; A61B 8/445; A61B 8/12; A61B 1/00177; A61B 8/5238; A61B 2090/3782; A61B 8/0883; A61B 17/03; A61F 2/2433; A61F 2/958; A61M 25/104
(Continued)

(56) References Cited

U.S. PATENT DOCUMENTS 3,520,293 A 7/1970 Atherholt
3,659,494 A 5/1972 Philbrick et al.
(Continued)

FOREIGN PATENT DOCUMENTS

WO 2012092167 A1 7/2012

OTHER PUBLICATIONS

Sep. 28, 2016 Office Action issued in U.S. Appl. No. 14/037,526.
(Continued)

*Primary Examiner* — Sanjay Cattungal
(74) *Attorney, Agent, or Firm* — Oliff PLC

(57) ABSTRACT

A mobile, hand-held communication device with a digital display, and a 3D camera for acquiring a three-dimensional image of the human body is programmed to function as a digital anthropometer. The user digitizes anatomical landmarks on the displayed image to quickly obtain anatomical measurements which are used with a known morphological relationship to make an anatomical prediction for clothing measurement, body composition, orthotic and insert manufacturing, and postural displacement with accuracy and without external equipment.

18 Claims, 15 Drawing Sheets

Related U.S. Application Data of application No. 13/336,123, filed on Dec. 23, 2011, now Pat. No. 8,721,567.

(60) Provisional application No. 61/427,286, filed on Dec. 27, 2010, provisional application No. 61/709,227, filed on Oct. 3, 2012, provisional application No. 61/942,813, filed on Feb. 21, 2014.

(51) Int. Cl.
*A61B 5/00* (2006.01)
*G01B 11/24* (2006.01)
*A61B 5/11* (2006.01)

(52) U.S. Cl.
CPC .......... *A61B 5/4561* (2013.01); *A61B 5/6898* (2013.01); *A61B 5/743* (2013.01); *G01B 11/24* (2013.01); *A61B 5/1116* (2013.01); *A61B 5/1128* (2013.01); *A61B 5/4869* (2013.01); *A61B 5/748* (2013.01); *A61B 2562/0219* (2013.01); *G06T 2207/10012* (2013.01); *G06T 2207/30196* (2013.01)

(58) Field of Classification Search
USPC .......... 345/645–680; 382/128–132; 600/407–480, 594
See application file for complete search history.

(56) References Cited

U.S. PATENT DOCUMENTS

| | | | |
|---|---|---|---|
| 4,603,486 A | | 8/1986 | Moroney et al. |
| 4,635,198 A | | 1/1987 | Hohlweck et al. |
| 4,786,925 A | | 11/1988 | Landwehr |
| 5,082,001 A | | 1/1992 | Vannier et al. |
| 5,947,742 A | * | 9/1999 | Katayama .......... A63B 24/0003 434/247 |
| 6,231,527 B1 | * | 5/2001 | Sol .................. A61B 5/1038 348/143 |
| 6,411,275 B1 | | 6/2002 | Hedberg |
| 6,423,015 B1 | | 7/2002 | Winkenbach et al. |
| 6,751,410 B1 | | 6/2004 | Stavely |
| 7,077,813 B2 | * | 7/2006 | Grace .................. A61B 5/4561 600/594 |
| 7,335,167 B1 | | 2/2008 | Mummy et al. |
| 7,366,559 B2 | | 4/2008 | Taicher et al. |
| 7,374,536 B1 | * | 5/2008 | Taylor .................. A61B 5/00 600/300 |
| 7,478,009 B2 | | 1/2009 | Cabrera et al. |
| 7,683,915 B2 | * | 3/2010 | Gunji .................. A61B 6/032 345/418 |
| 7,742,073 B1 | | 6/2010 | Cohen-Solal et al. |
| 7,761,233 B2 | | 7/2010 | Schott et al. |
| 7,796,871 B2 | | 9/2010 | Park et al. |
| 7,796,872 B2 | | 9/2010 | Sachs et al. |
| 7,876,320 B2 | * | 1/2011 | Marugame .......... G06T 17/10 345/419 |
| 7,957,784 B2 | | 6/2011 | Voth et al. |
| 8,209,240 B2 | * | 6/2012 | Ryu .................. G06Q 30/00 705/26.61 |
| 8,721,567 B2 | | 5/2014 | Ferrantelli |
| 2002/0116990 A1 | * | 8/2002 | Claussen .......... A61B 5/1121 73/65.01 |
| 2003/0076408 A1 | | 4/2003 | Dutta |
| 2004/0186395 A1 | | 9/2004 | Vastano |
| 2006/0072019 A1 | | 4/2006 | Stavely et al. |
| 2006/0203131 A1 | * | 9/2006 | Gunji .................. A61B 6/032 348/739 |
| 2007/0083384 A1 | * | 4/2007 | Geslak .............. G06Q 10/00 705/2 |
| 2007/0135737 A1 | | 6/2007 | Vastano |
| 2007/0230829 A1 | | 10/2007 | Sirohey et al. |
| 2008/0009773 A1 | | 1/2008 | Harrison et al. |
| 2008/0030464 A1 | | 2/2008 | Sohm et al. |
| 2008/0031512 A1 | * | 2/2008 | Mundermann .... G06K 9/00342 382/154 |
| 2008/0044169 A1 | | 2/2008 | Wernersson |
| 2008/0200841 A1 | | 8/2008 | Di Mascio et al. |
| 2009/0046140 A1 | | 2/2009 | Lashmet et al. |
| 2009/0062693 A1 | | 3/2009 | Woolfson et al. |
| 2009/0262989 A1 | * | 10/2009 | Kozakaya .......... G06K 9/00281 382/118 |
| 2010/0002015 A1 | * | 1/2010 | Handa .................. G01C 21/20 345/650 |
| 2010/0004539 A1 | * | 1/2010 | Chen .................. A61B 8/0825 600/445 |
| 2010/0077857 A1 | | 4/2010 | Ye |
| 2010/0078479 A1 | | 4/2010 | Epshteyn |
| 2010/0138194 A1 | | 6/2010 | You et al. |
| 2010/0141784 A1 | * | 6/2010 | Yoo .................. H04N 5/23219 348/222.1 |
| 2011/0009776 A1 | | 1/2011 | Woolfson et al. |
| 2011/0015513 A1 | | 1/2011 | Mura Yanez |
| 2011/0135165 A1 | | 6/2011 | Wechsler et al. |
| 2011/0251903 A1 | * | 10/2011 | Ryu .................. G06Q 30/00 705/14.73 |
| 2012/0040717 A1 | | 2/2012 | Levy et al. |
| 2012/0165647 A1 | | 6/2012 | Kang et al. |
| 2012/0165648 A1 | | 6/2012 | Ferrantelli |
| 2012/0235993 A1 | * | 9/2012 | Kim .................. A61B 6/032 345/419 |
| 2013/0324850 A1 | * | 12/2013 | Petruzzelli ............ A61B 8/467 600/443 |
| 2014/0031700 A1 | | 1/2014 | Ferrantelli |
| 2014/0267611 A1 | * | 9/2014 | Kennett ............ G06K 9/00335 348/46 |

OTHER PUBLICATIONS

Feb. 24, 2015 Search Report Issued in Canadian Application No. 2,822,244.
International Search Report and Written Opinion, PCT/US2011/067111, dated Apr. 25, 2012.
International Preliminary Report on Patentability, PCT/US2011/067111, (dated Jan. 9, 2013).
"Prediction of Percent Body Fat for U.S. Navy Men From Body Circumference and Height", Report No. 84-11, Hodgdon, J.A. and Beckett, M.B., 1984, Naval Health Research Center, San Diego, CA, 26 pages.
"Body Composition in Military Services: Standards & Methods", Report No. 90-21, Hodgdon, J.A., 1990, Naval Health Research Center, San Diego, CA, 18 pages.
"The Army Weight Control Program", Army Regulation 600-9, Nov. 27, 2006, Headquarters, Department of the Army, Washington, D.C. 55 pages.
"Waist Circumference and Waist-Hip Ratio, Report of a WHO Expert Consultation", Dec. 8-11, 2008, World Health Organization, Geneva, Switzerland, 14 pages.
Department of Defense publication DODI 1308.3, Nov. 5, 2002, 41 pages.
Hodgdon, J.A. and M. B. Beckett (1984) Prediction of Percent Body Fat for U.S. Navy Men from Body Circumferences and Height, Report No. 84-11, Naval Health Research center, San Diego, CA.
Hodgdon, J.A., Body (1990) Composition in the Military Services: Standards & Methods, Report No. 90-21, Naval Health Research Center, San Diego, CA.
Feb. 25, 2016 Office Action issued in U.S. Appl. No. 14/037,526.
Jan. 20, 2017 Office Action issued in U.S. Appl. No. 14/037,526.

* cited by examiner

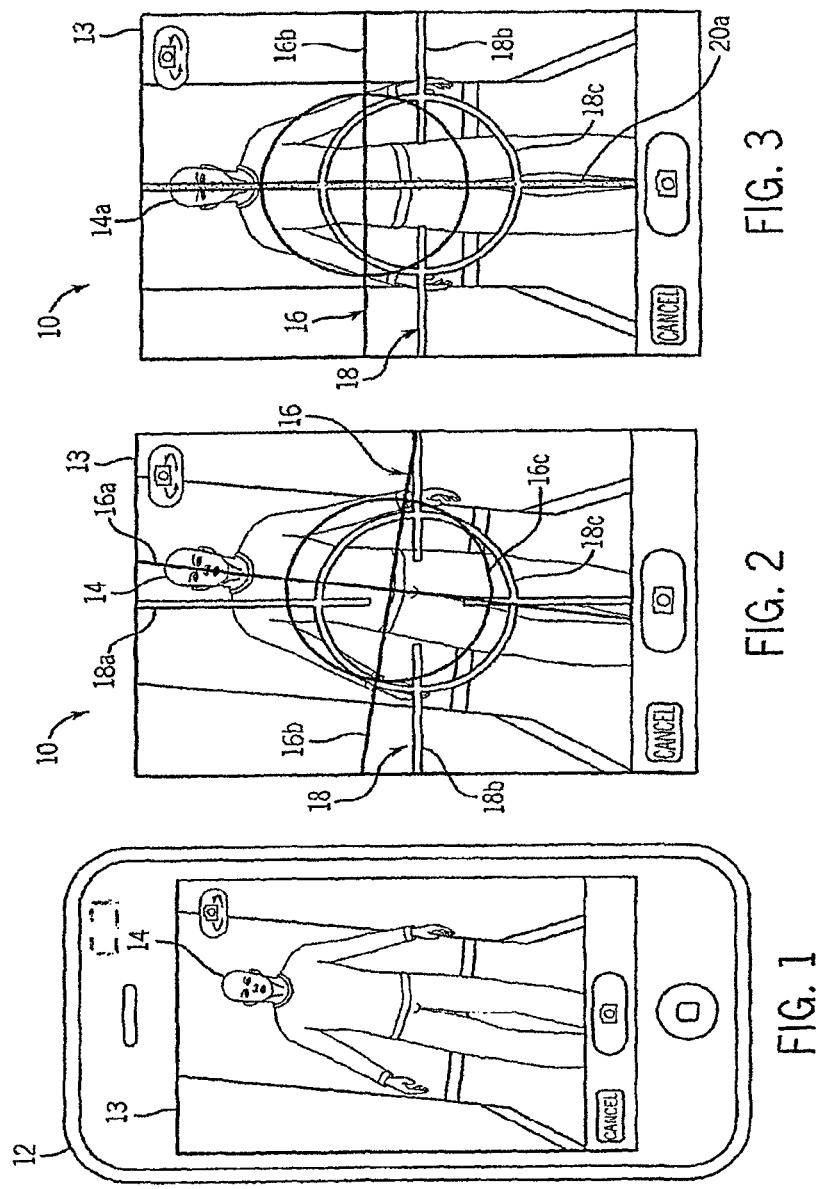

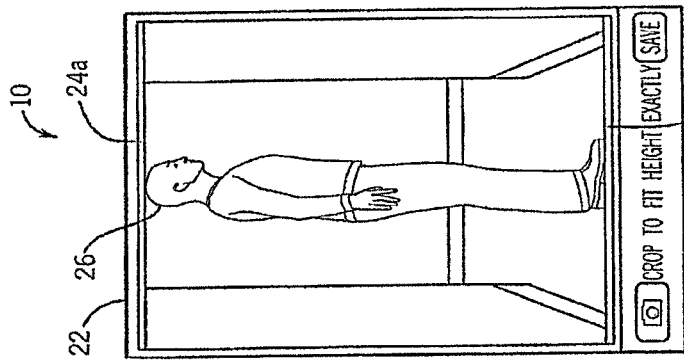
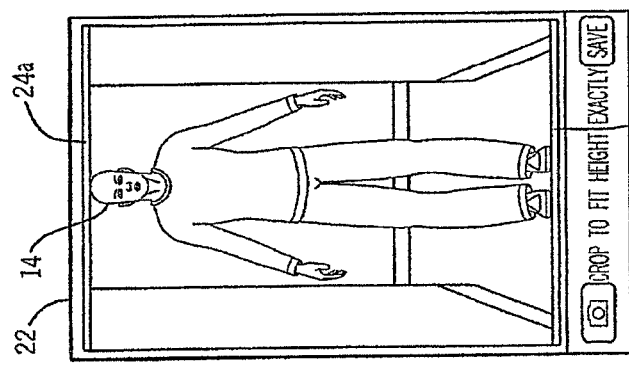
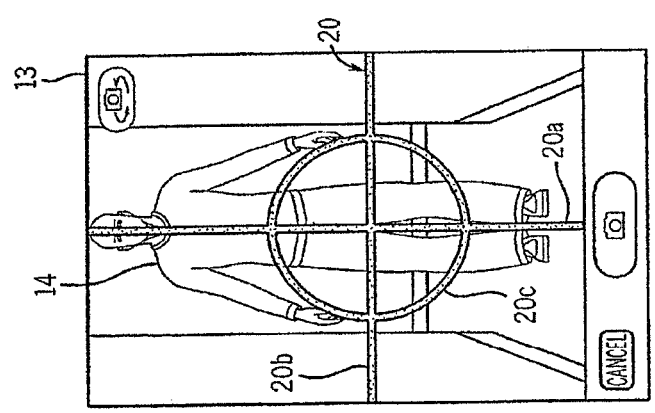

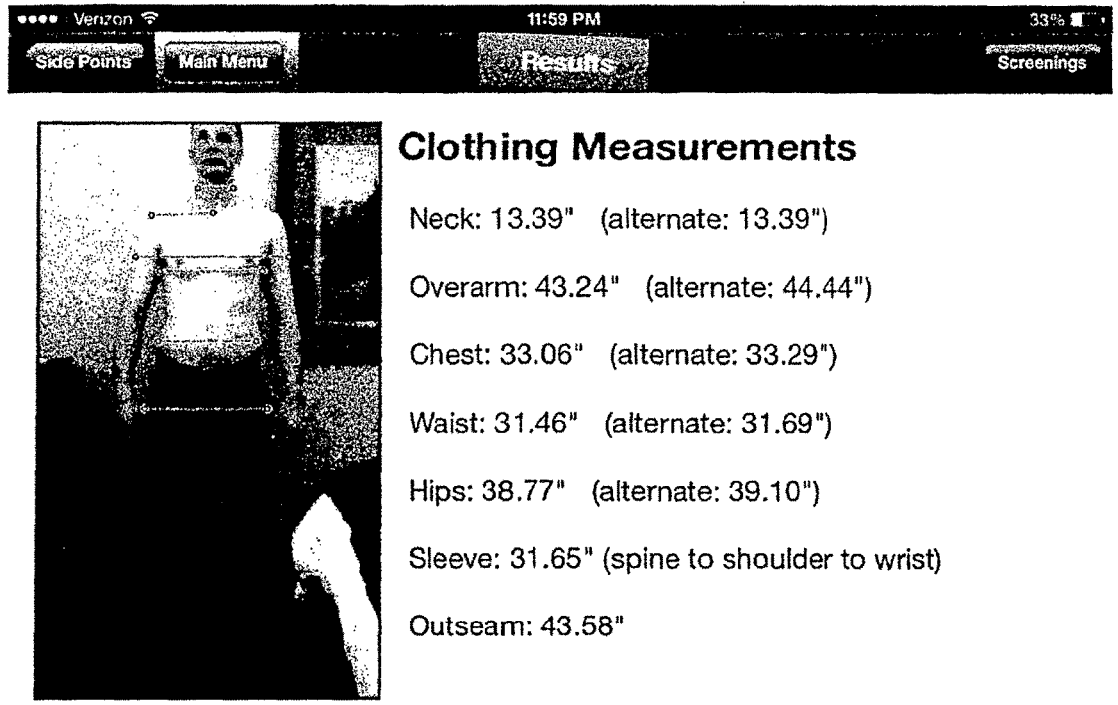

Clothing Measurements

Neck: 13.39"  (alternate: 13.39")

Overarm: 43.24"  (alternate: 44.44")

Chest: 33.06"  (alternate: 33.29")

Waist: 31.46"  (alternate: 31.69")

Hips: 38.77"  (alternate: 39.10")

Sleeve: 31.65" (spine to shoulder to wrist)

Outseam: 43.58"

2D Linear Measurements

Spine to Shoulder: 7.40" linear
Front Neck: 4.23" linear,  13.30" circ
Front Overarm: 18.03" linear,  56.63" circ
Front Chest: 12.22" linear,  38.40" circ
Front Waist: 11.67" linear,  36.65" circ
Front Hips: 14.55" linear,  45.71" circ Shoulder to Elbow: 13.40" linear
Elbow to Shoulder: 10.85" linear
Side Neck: 4.29" linear,  13.48" circ
Side Chest: 8.68" linear,  27.25" circ
Side Waist: 8.21" linear,  25.79" circ
Side Hips: 9.91" linear,  31.12" circ
Outseam: 43.58" linear

FIG.17

LeanScreen Report for Cheryl Smith

The following report provides details about your percentage of body fat (PBF: 21%), Body Mass Index (BMI: 21.6), waist to hip ratio (WHR: 0.8), lean body mass (LBM: 96.4 lb), and Basal Metabolic Rate (BMR: 1312.60). All of these values are important indicators of your health.

Your Front FatScreen Profile          Your Side FatScreen Profile

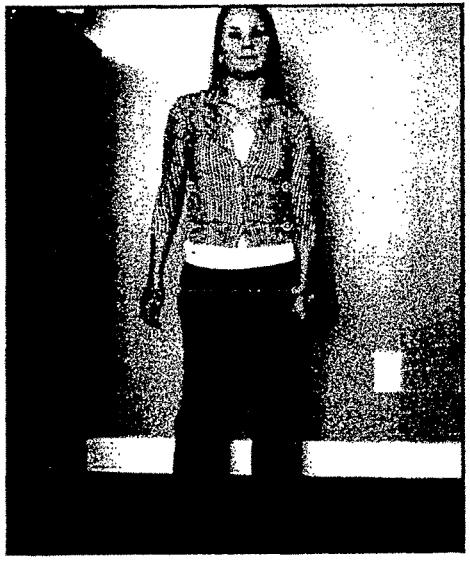 

| General Body Fat Percentage Categories | |
|---|---|
| Essential Fat | up to 13% |
| Athletes | 14 - 20% |
| Fitness | 21 - 24% |
| Acceptable | 25 - 31% |
| At Risk | 32% + |

Average Body Fat: 21%

Body fat percentage is a measurement of your individual calculated body composition. The percentage of body fat (PBF) is the actual percentage of your toal weight that is not bone, muscle, or body fluid. Your PBF has been calculated with LeanScreen. You weigh 122 lb and your body fat percentage (PBF) is approximately 21% calculated by your anatomical measurements. Health body fat percentages vary on your age, gender and body type, however there are some general guidelines as observed in this table.

FIG. 19

METHOD AND SYSTEM FOR POSTURAL ANALYSIS AND MEASURING ANATOMICAL DIMENSIONS FROM A DIGITAL THREE-DIMENSIONAL IMAGE ON A MOBILE DEVICE

RELATED APPLICATIONS

This application claims priority under 35 USC §119 of U.S. Provisional Application No. 61/942,813, filed Feb. 21, 2014, and this application is a continuation in part application of co-pending U.S. application Ser. No. 14/037,526, filed Sep. 26, 2013, which in turn claims priority under 35 USC §119 of U.S. Provisional Application No. 61/709,227, filed Oct. 3, 2012, and is a continuation in part application of U.S. application Ser. No. 13/336,123, filed Dec. 23, 2011 (now U.S. Pat. No. 8,721,567), which in turn claims priority under 35 USC §119 of U.S. Provisional Application 61/427,286, filed Dec. 27, 2010. The entire contents of the prior applications are hereby incorporated by reference in there entireties.

TECHNICAL FIELD

The present invention relates to a method and system for measuring anatomical dimensions from a digital image, and particularly in one embodiment, a three-dimensional image on a mobile device or computer. Disclosed embodiments relate particularly to postural screening, measurements for clothing, estimating body composition such as body fat analysis, and measurements for orthotics or insert manufacturing.

BACKGROUND AND SUMMARY

Currently, using a tape measure or caliper anthropometer, an examiner has to manually record measurements of human body part dimensions in length as well as in circumference. The measurements are needed in the clothing industry for fitting cloths, in postural screening and in many other aspects of today's health care system and in the fitness industry where the measured body dimensions are used in calculation of body ratios to derive estimation of body composition. There is a need for an improved method and system that allow more efficient measurements of the dimensions of the human body.

A known postural screening method involves a person/patient standing in a framework between a vertical plumb line and a vertically oriented, planar backdrop having a grid-work of vertical and horizontal lines. The medical practitioner performing the screening then observes and measures postural deviations (mal-alignments) of the patient in the frontal plane, sagittal plane and transverse plane relative to the vertical and horizontal lines on the backdrop and the plumb line. The postural deviations observed and measured are then recorded on a postural evaluation chart. The data from the postural evaluation can be input to a computer to aid in analysis in selection of a corrective exercise program, for example. U.S. Pat. No. 7,077,813 discloses such a system and method. A similar method is employed in U.S. Published Patent Application No. US 2007/0083384 A1 where overlays of a vertical line, an orthogonal grid, horizontal reference lines, and indicators are placed on a computer-displayed image of the body to aid posture analysis where external equipment is used initially in obtaining the image.

Drawbacks of the known methods and systems include that taking all the postural deviation measurements can be time consuming and imprecise. In addition, the need for external equipment in the analysis or obtaining the patient image can dictate that the screening must be conducted in a facility having the required framework of vertical backdrop and plumb line or other equipment. There is a need for an improved method and system for measuring anatomical dimensions which overcome these drawbacks and limitations. The present invention addresses this need.

The improved method for measuring the dimensions of the human body of the present invention comprises providing a digital anthropometer on a mobile device, and digitizing anatomical landmarks on a digital image, and in particular a digital three-dimensional image of the human body displayed with established calibration methods for measuring dimensions of the human body. A disclosed embodiment of the system of the invention for practicing the method comprises a programmed device including a digital touch screen display having an array of pixels, a camera for acquiring an image of a person on the digital touch screen display, and means for digitizing anatomical landmarks on an image of a person displayed on the digital touch screen display for measuring dimensions of the human body. The camera can be a 3D camera providing a 3D image of the person on the display. The method for measuring and system of the invention using a digital image, particularly a two-dimensional image is disclosed in my copending U.S. patent application Ser. No. 14/037,526 filed Sep. 26, 2013, which is incorporated herein by reference.

The programmed device in one embodiment is a mobile, hand-held communication device having at least one positional device selected from the group consisting of a gyroscope, an accelerometer, and a level to level the camera. With the device, the method for measuring includes activating the at least one positional device and using an output thereof for leveling the camera before capturing the image.

The display screen in the several embodiments is preferably a touch screen for the purpose to quickly identify coordinates of the selected anatomical landmarks of the body image displayed on the screen, e.g. to digitize the anatomical landmarks for calculation of linear distances by the programmed computer of the device. These features advantageously reduce the time for measuring the dimensions and the accuracy, without the need for external equipment or special facilities.

The disclosed system further includes means for making an anatomical-prediction using the measured dimensions and a known morphological relationship. Known mathematical formulae expressed in the computer program of the device relate the measured dimensions to the anatomical prediction. According to an aspect of the invention, the anatomical prediction includes at least one of circumference and volume of a body part which may be displayed on the display screen. In one disclosed embodiment the anatomical prediction is a clothing measurement selected from the group consisting of neck, overarm, chest, waist, hips, sleeve and outseam. According to another embodiment the anatomical prediction is a body composition. In a further embodiment a postural displacement is predicted from the measured dimensions and known morphological relationship. The disclosed system can also be used to obtain an image or images of the foot for use in orthotic and insert manufacturing.

Thus, in use of the system the present invention includes a method of deriving an anatomical prediction using a known morphological relationship and a programmed appa-} ratus including a digital touch screen display and means for acquiring an image of a person on the digital touch screen display, the method comprising acquiring an image of a person on the digital touch screen display, digitizing points on a plurality of anatomical landmarks on the displayed image, determining linear anatomical dimensions of the person's body using the digitized points and a scale factor for the displayed image, and making an anatomical prediction using the determined linear anatomical dimensions and a known morphological relationship. In one embodiment the anatomical prediction is a clothing measurement. In another embodiment the anatomical prediction is body composition. In a further embodiment the anatomical prediction includes at least one of circumference and volume of a body part. In a still further embodiment the anatomical prediction is a postural displacement or is used for fitting/manufacturing an orthotic or insert for the foot. To further exemplify the use of the 3D acquired images in orthotic manufacturing and clinical fitting, it is noted that in the past a practioner such as a therapist or podiatrist typically must cast a patient's foot either weight bearing or non-weight bearing positions to have the ability to capture the exact dimensions and form of the foot for orthotic manufacturing. Now instead of using a pin-type mold system, foam based or plaster type fitting system, in accordance with the method and system of the invention a true 3D image can be acquired and a proper orthotic manufactured therefrom saving considerable time and money to the practioner. Ultimately, the 3D data may also be used by a 3D type 'printer' and an orthotic literally 'printed' based on 3D data.

For postural analysis in accordance with the present invention, the 3D captured images have the advantage of traditional multi-camera systems but being much less expensive and mobile. Another advantage of 3D postural assessment in accordance with the invention is that the end user practioner can pan-zoom in any rotational view of the posture and then click precise anatomical landmarks and planes which the system can compare to one another to generate axial rotation (which is not easily calculated from 2D photographs with a single camera).

For clothing fitting and body composition assessment, using a 3D image in accordance with the disclosed method, exact circumferential measurements can easily be derived with the 3D data from the Kinect or Structure type3D camera/sensor. Clicking known locations permits one to generate measurements of body parts and/or regions for exact anthropometric data from which can be extrapolated exact clothing fitting or precise body part mesaurements usually tracked in health and fitness. For example, personal trainers measure arms, legs and body girth of torso to track weight loss and "inches lost". Further, using exact circumferential data, a more precise method of anthropometric body composition analysis is possible using known methods pioneered by the U.S. Department of Defense as discussed hereinafter.

In the disclosed embodiments, the method further comprises acquiring at least two different views of the person as images on the digital touch screen display and/or a digital three-dimensional image of the person, which can be rotated to provide each of said at least two different views, digitizing points on anatomical landmarks on each displayed image and determining linear anatomical dimensions of the person's body using the digitized points and a scale factor for each displayed image for making the anatomical prediction. In the disclosed embodiments the views acquired include at least a front view and a side view of the person and/or a digital three-dimensional image of the person which can be rotated to provide each of the front and side views.

An embodiment of the invention particularly relating to measuring dimensions for postural screening is disclosed but is understood as instructive with respect to the other embodiments disclosed herein taken with the additional disclosure relating to each of the other embodiments.

The improved postural screening method according to the example embodiments of the present invention comprises acquiring an image of a patient on a display screen having an array of pixels, determining a pixel to distance ratio for the displayed image, and calculating a postural displacement of the patient in the displayed image using the determined ratio. The standing framework of vertical backdrop and plumb line or overlaid grid-work of lines of the prior art are not necessary. According to the disclosed method, a known linear distance in the displayed image and the number of display screen pixels spanning the distance are used in determining pixel to distance ratio. The known linear distance in an example embodiment is the height of the patient. Alternately, or in addition as a secondary calibration, a marked distance can be provided in the acquired image of the patient, as by the use of a meter stick in the image or other markings of a known distance apart, to provide a known linear distance.

The postural screening method in example embodiments further includes scaling the size of the image relative to the display screen to normalize the known linear distance in the image to a display screen reference distance corresponding to a known number of pixels for determining the pixel to distance ratio. According to a disclosed method, at least one reference line is provided over the displayed image to demark the display screen reference distance.

The method as disclosed herein further includes displaying a reference line overlaid on the screen providing vertical, horizontal and center references, providing a corresponding reference line anchored to the displayed patient's image, and adjusting the image in the display so that the two reference lines are aligned before determining the pixel to distance ratio.

The patient's image can be acquired by accessing a database. Alternatively, the person performing the screening can operate an image capture device of a camera for acquiring the image of the patient. Either a two-dimensional camera providing a 2D image or a three-dimensional camera providing a 3D image can be used. The method preferably includes leveling the image capture device before capturing the image from which the pixel to distance ratio is to be determined for eliminating distortion. According to the example embodiments, the image capture device and display screen are part of a mobile, hand-held communication device having at least one positional device selected from the group consisting of a gyroscope, an accelerometer, and a level. The method includes activating the at least one positional device and using an output thereof to provide a reference for leveling the image capturing device. Using the 3D type cameras such as Kinect or Structure sensor by Occipital, the 3D camera is tethered to the mobile device directly or via wireless transmission, and provides calibrated 3D images on all three axes from which anatomical dimensions and postural deviations can be derived.

In disclosed embodiments, the method further includes displaying a reference line on the display screen over the acquired image, performing panning to center the image on the screen, and performing zooming to fit the image in the reference line before determining the pixel to distance ratio. Still further, the method comprises providing anatomical landmarks on the acquired image of the patient to facilitate calculating a postural displacement. The display screen is a touch screen for this purpose to identify coordinates for calculation of postural displacements by the programmed computer of the mobile, hand-held communication device. An advantage of the 3D acquired images in the method and system of the invention is that from these the operator can easily predict axial rotations of different body regions compared with 2D image acquisition which would typically require obtaining multiple photographs from every side as well as axial (above the head or below the feet) to generate information needed to assess three dimensional postural analysis.

A system for performing postural screening according to the invention comprises means for acquiring an image of a patient on a display screen having an array of pixels, means for determining a pixel to distance ratio for the displayed image and means for calculating a postural displacement of the patient in the displayed image using the determined ratio. The means for acquiring an image of a patient according to an example embodiment includes an image capture device of the mobile, programmed, hand-held communication device, for capturing at least one of a 2D image or a 3D image of the person on the digital touch screen display. Preferably, the device includes at least one positional device selected from the group consisting of a gyroscope, an accelerometer, and a level which provides a reference for leveling the image capturing device. The system further includes means for panning a displayed image on the screen to center the image on the screen, and means for zooming to fit a displayed image in a reference line on the display screen. Means are provided for displaying at least one reference line over the displayed image to demark a display screen reference distance corresponding to a known number of pixels for determining the pixel to distance ratio. In the case of the use of a known 3D camera, the 3D system camera automatically calibrates using an infrared or other type sensor so additional calibration of the image as described herein with respect to a 2D camera image may be unnecessary.

The system of disclosed embodiments further includes means for displaying a reference line overlaid on the screen providing vertical, horizontal and center references, means for displaying a corresponding reference line anchored to the displayed patient's image, and means for aligning image and display screen reference lines before determining the pixel to distance ratio. The system further includes means for providing anatomical landmarks on the acquired image of the patient to facilitate calculating a postural displacement.

The present invention further includes a machine-readable medium containing at least one sequence of instructions that, when executed, causes a machine to: calculate at least one postural displacement of a patient from a displayed image of the patient on a display screen having an array of pixels, using a determined pixel to distance ratio for the displayed image.

These and other objects, features and advantages of the invention will become more apparent from the following detailed description of example embodiments taken with the accompanying drawings.

BRIEF DESCRIPTION OF DRAWINGS

FIG. 1 is a front perspective view of a mobile communication device with an image capturing device in the form of a camera on the back side, shown in dashed lines, of the device for acquiring an image of a patient and, as shown, a display screen on the front opposite side having a two-dimensional array of pixels on which the image as seen on the camera is displayed.

FIG. 2 is a front perspective view of the screen of the device of FIG. 1 showing a step of the postural screening method wherein a reference line is overlaid the image providing vertical, horizontal and center references on the display screen and wherein a corresponding reference line is anchored to the displayed patient's image.

FIG. 3 is a front perspective view of the screen of the device of FIG. 1 showing another step of the postural screening method wherein the two reference lines in FIG. 2 have been aligned in the vertical or sagittal plane by rotation of the device relative to the patient being viewed by the camera.

FIG. 4 is a front perspective view of the screen of the device of FIG. 1 showing a further step of the postural screening method wherein the two reference lines in FIG. 3 have been aligned in the vertical plane by tilting the device at the top toward the patient to level the image capturing device.

FIG. 5 is a front perspective view of the screen of the device of FIG. 1 showing another step of the postural screening method wherein two spaced horizontal lines are displayed on the screen at the top and bottom and the image has been centered by panning and scaled by zooming with the camera to fit the image precisely in the reference distance defined between the two lines to normalize the height of the image to a screen distance corresponding to a known number of pixels spanning the distance in the vertical direction.

FIG. 6 is a front perspective view of the screen of the device of FIG. 1 showing an image of the patient like that of FIG. 5 but in the direction of the frontal plane of the patient.

FIG. 17 illustrates and lists two dimensional linear measurements made with the mobile device of the invention during the steps in the flow-chart of FIG. 16 and listing the clothing measurements calculated for fitting a tuxedo using the measurements and known mathematical formulae.

FIG. 19 is a front view and a side view of a subject depicting digitized anatomical landmarks on the image and illustrating linear measurements made in the views of the subject in accordance with the steps of the flow chart of FIG. 18, the views being shown as part of a report on the results of calculation of an estimate of average body fat using the measurements.

FIG. 20A being a posterior oblique view depicting a left cervical list and right skull flexion relative to plane of the shoulders, and also showing right shoulder lateral flexion.

FIG. 20B is a side view oblique where a anterior cervical list and a thoracic posterior extension is noted.

FIG. 20C is a "bird's eye" view depicting right skull rotation relative to plane of shoulders, and a right "rib hump" posture common in scoliosis.

FIG. 20D is a frontal view with slight oblique depicting and measuring left head list with right skull flexion and right head rotation relative to plane of shoulders, also showing subtle right shoulder flexion.

DETAILED DESCRIPTION

Figure 8:
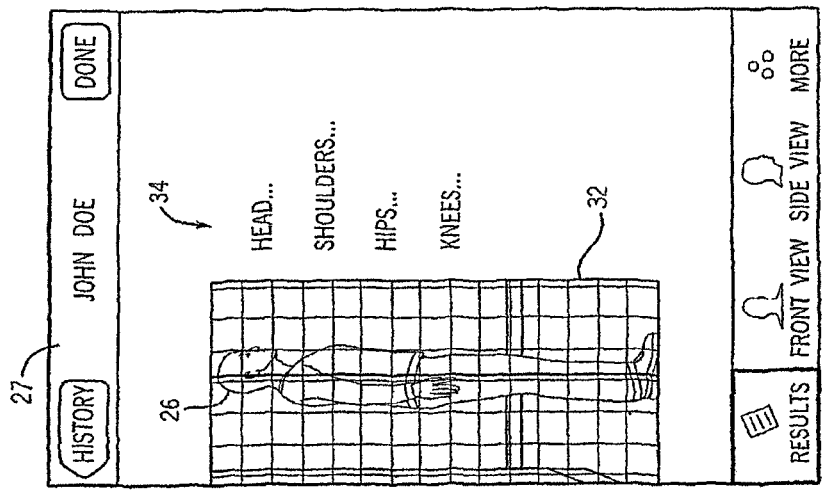
FIG. 8 is a front perspective view of the screen of the device of FIG. 1 wherein the image acquired in FIG. 6 optionally is displayed behind a grid overlay of vertical and horizontal lines against which a qualitative view of postural displacement is observed.
Figure 7:
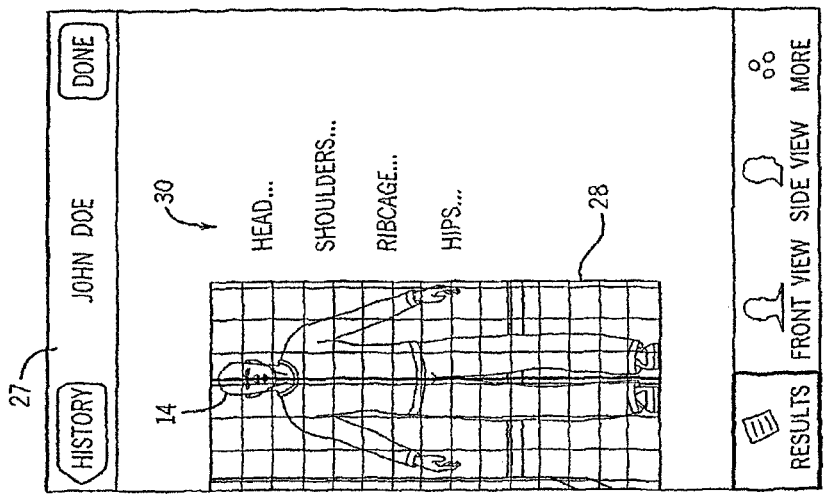
FIG. 7 is a front perspective view of the screen of the device of FIG. 1 wherein the image acquired in FIG. 5 optionally is displayed behind a grid overlay of vertical and horizontal lines against which a qualitative view of postural displacement can be observed.

The following detailed description taken with the accompanying drawings is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide a method for determining an anatomical measurement of the human body such as measuring the dimensions of the human body comprising providing a digital anthropometer on a mobile device, and digitizing anatomical landmarks on a displayed image such as a photograph or digital three-dimensional image of the human body displayed on the device with established calibration methods for measuring dimensions of the human body. And broadly, the embodiments of the prevention provide a digital anthropometer device or system using digitization of anatomical landmarks on a displayed image such as a photograph or digital three-dimensional image with established calibration methods. The device/system is designed for measuring the dimensions of the human body and comprises a programmed device including a digital display, a touch screen in the example embodiments having an array of pixels and a camera for acquiring an image of a person on the digital touch screen display, and means for digitizing anatomical landmarks on an image of a person displayed on the touch screen display for measuring dimensions of the human body.

An embodiment of the invention also enables the ability to derive the anatomical measurement such as the linear measurement or an angular measurement from the anterior, posterior and lateral aspects or 3D view of a body part, and then calculate an estimate of circumference and volume of that body part using mathematical equations.

The invention also enables recording a linear distance and subsequent circumferential and volume calculations utilizing mathematical formulae which can also be tracked by software. The measurements can also be superimposed on the digital image of the person displayed on the device.

Another embodiment of the invention can produce reports for education on body posture, measurements for clothing, or for example body composition as explained and shown with reference to FIGS. 11-19 below. This could be used by fitness professionals, health care professionals, or clothing industry professionals or where an anatomical measurements need to be calculated by using prediction from digitizing anatomical points on/from a digital picture.

Once the images are obtained and digitized following protocols of the disclosed methods, digitization points on anatomical landmarks for purposes of posture, linear and circumferential anthropometric measurements can be performed. After these measurements are obtained, body ratios can be calculated to predict a person's body composition using well known anthropometric morphological relationships.

An exemplary embodiment of the invention may be utilized in health care, fitness or the clothing industry, to measure posture, to measure the foot for manufacturing orthotics and inserts, and to calculate body dimensions, shape, posture, and body composition based on anatomical ratio relationship, and to track progress of linear, angular and circumferential measurements. In other industries such as clothing, one can obtain images, and find measurements needed to for example fit a person for a suit or tuxedo instead of using manual tape measuring. The images used can be two-dimensional or three-dimensional images A first embodiment is a postural screening method comprising acquiring patient information, acquiring an image of a patient, displaying a reference line overlaid on the acquired image for scaling the acquired image, providing panning to center the acquired image, providing zooming to fit the image within the displayed reference lines, for normalizing the patient's height, determining a pixel to distance ratio using the acquired patient information and the normalized patient height, calculating postural displacements, and presenting a postural analysis. Aspects of the present invention provide a postural screening method that may be implemented on a mobile, hand-held communication device that incorporates the device's gyroscope, accelerometer, and camera. The camera may be either a 2D camera or a 3D camera such as a Kinect by Microsoft, a Kinect type camera, a Structure Sensor by Occipital, or any similar technology.

Referring now to FIG. 1, a front perspective view of a mobile, hand-held communication device 12 is shown, which on one side has a screen 13 capable of displaying a frontal image 14 of a patient being viewed with a camera or image capture device on an opposite side. The device in the embodiment is an Apple iPhone 4 the computer of which is programmed in accordance with the invention as described hereinafter to perform the disclosed postural screening method. Other mobile, hand-held communication devices capable of running a program in accordance with the invention could also be used, such as iPhone®, iPod Touch®, iPad® and Android® devices including tablets and Windows® based tablets. FIGS. 2-8 show front perspective views of screen 13 showing steps of a posture screening method according to an embodiment of the present invention. Reference will be made to FIGS. 1-8 in the following description of the postural screening method.

Figure 9:
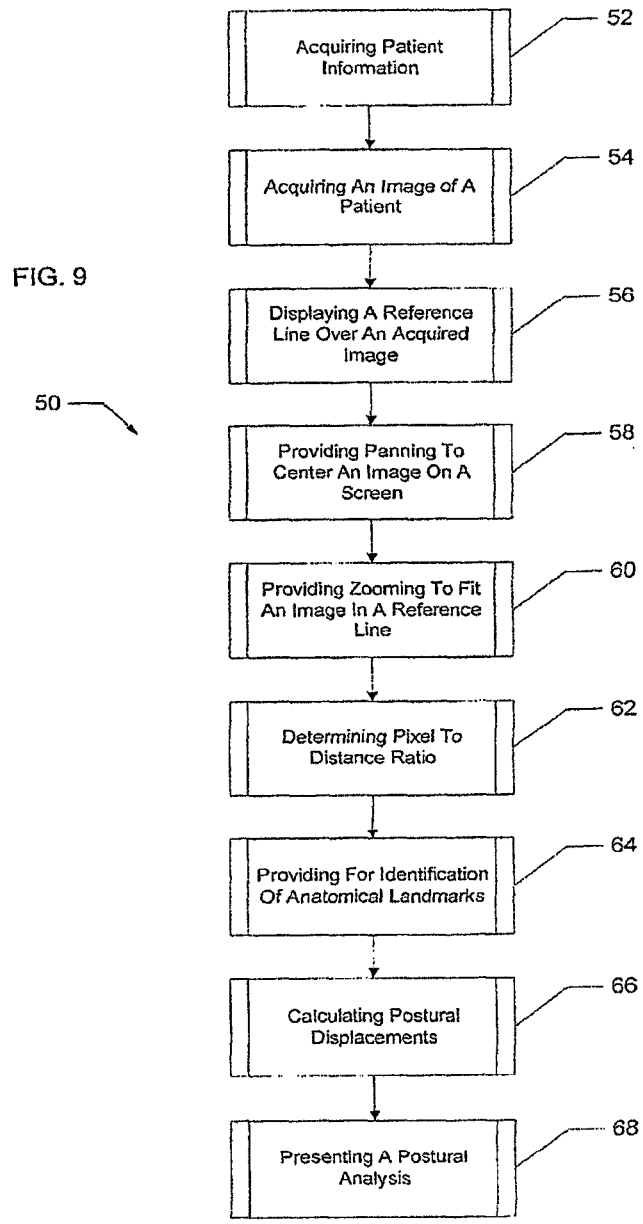
FIG. 9 is a process flow diagram of a method of postural screening according to an example embodiment of the present invention.

Referring now to FIG. 9, a postural screening method 50 is shown according to an embodiment of the present invention. Method 50 in the example embodiment includes a step 52 of acquiring patient information, which may include, for example, accessing a database or prompting a user to enter information. Acquired information in may include, for example, height, weight, sex and age of a patient.

Figure 10:
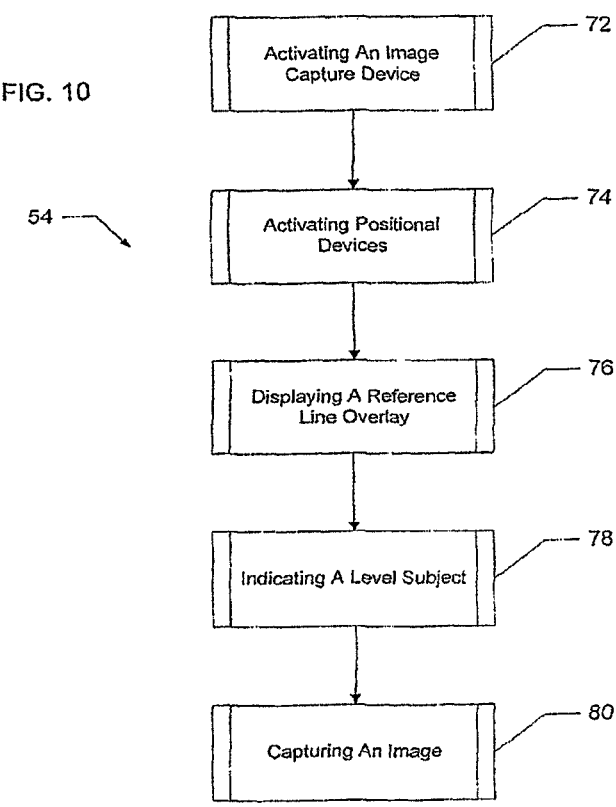
FIG. 10 is a process flow diagram of acquiring an image of a patient with the device of FIG. 1.

Method 50 may include a process 54 of acquiring an image of the patient. Referring now to FIG. 10, a process flow diagram of process 54 of acquiring a frontal image 14 of the patient is shown. Process 54 as disclosed includes a step 72 of activating an image capture device, in this case the camera of the iPad 4. Process 54 in the embodiment includes a step 74 of activating a positional device, namely one or more of a gyroscope, an accelerometer, and a level in the device. The positional device(s) is used in accordance with the present invention to provide feedback to a user as to whether the image capture device is level.

Process 54 includes a step 76 of displaying a reference line overly 18 on screen 13. The reference line overlay 18 may aid a user in aligning the patient in the field of view of the image capture device by providing, for example, a vertical reference 18a, a horizontal reference 18b, and a center reference 18c. Process 54 includes a step 78 if indicating a level patient. According to the embodiment of the present invention, in step 78 a visual indication including, for example, corresponding references 16a, 16b, and 16c, are provided anchored to frontal image 14. An aligned frontal image 14 may have a reference line 20, which may have vertical, horizontal, and center reference lines 20a, 20b, and 20c, which may, for example, change colors indicating alignment. Process 54 may also include a step 80 of capturing an image, for example, once alignment is achieved. In an exemplary embodiment of the present invention, a plurality of images may be acquired including, for example, frontal image 14, lateral image 26, and a rear perspective image.

According to a variation of the embodiment of the present invention, process 54 may include accessing a data storage device. The data storage device may include, for example, a picture roll or album, which may contain a previously captured image of the patient. As another variation, the process 54 for acquiring an image of a patient may include capturing a three-dimensional image of the person by means of a 3D camera of the device 12 to display a digital three-dimensional image of the person on the digital touch screen. This would involve taking several different views of the person as by scanning, for example. The user can pan and zoom and rotate the three-dimensional displayed image to analyze the subject in any plane by means of computer input devices as discussed below.

Referring again to FIG. 9 method 50 may include a step 56 of displaying an upper reference line 24a and a lower reference line 24b over a display 22 of frontal image 14 and a lateral image 26 of the patient. The two spaced parallel lines are spaced apart a reference distance corresponding to a known number of pixels of screen 13. The displayed reference lines 24a and 24b may be used as a reference for aligning or normalizing the images 14 and 26, which may require positioning or scaling. Hence, method 50 may include a step 58 of providing panning capability of the acquired image to a user, and a step 60 of providing zoom capability of the acquired image to a user. The provided panning capability may allow a user to properly center or rotate images 14 and 26 to fit in reference lines 24a and 24b. The provided zoom capability may allow a user to properly size an acquired image to fit it within reference lines 24a and 24b for normalizing the height of the patient in the acquired image and establishing a pixel height of the patient. Method 50 may include a step 62 of determining a pixel-to-distance ratio, which may be a quotient calculated by dividing a pixel height of images 14 and 26 divided by a patient's height.

Figure 13:
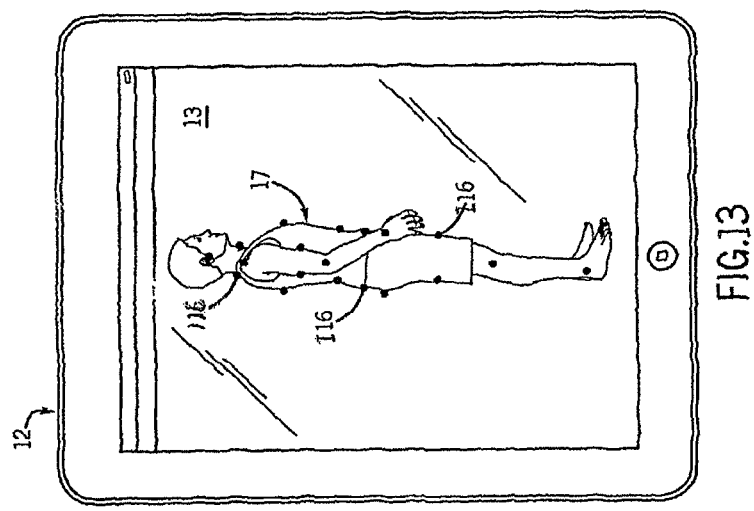
FIG. 13 is an alternate view of an exemplary embodiment of the invention similar to FIG. 12, but illustrating a side view of the subject.
Figure 12:
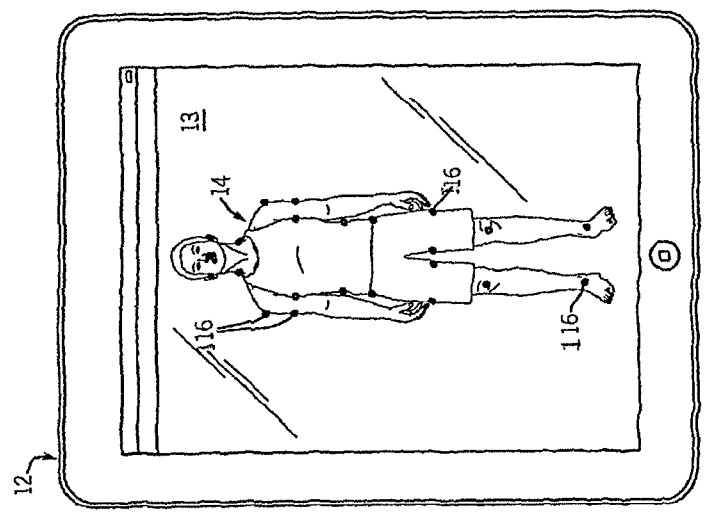
FIG. 12 is a front elevation view of an exemplary embodiment of the invention, illustrating a front view of the subject depicted on the digital touch screen display of the mobile device of the invention.
Figure 14:
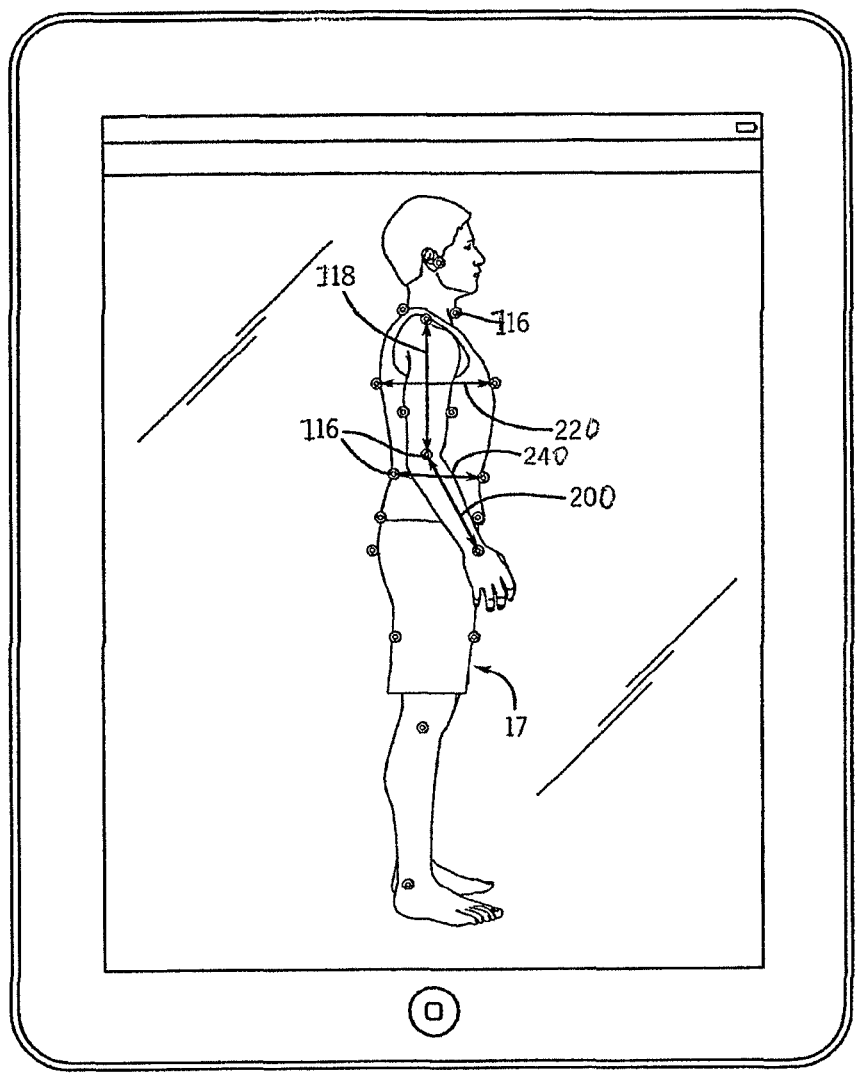
FIG. 14 is an alternate view of an exemplary embodiment of the invention, illustrating a side view of the subject on the display of the device of the invention with the measurements being made.

Method 50 may include a step 64 of providing for identification of the patient's anatomical landmarks, wherein a user may be prompted to identify locations of a plurality of anatomical landmarks on the acquired image of the patient by touching the touchscreen of the device to identify an anatomical landmark. The plurality of the landmarks may correspond, for example, to skeletal landmarks, bone markings, or joints. The identified plurality of landmarks may be used with the known pixel to distance ratio for the displayed image to calculate absolute distances and relative spatial positioning thereof, and may be used in an analysis of the patient's posture. In an exemplary embodiment of the present invention, the selection of anatomical landmarks may be on a plurality of images 14 and 26. The images of FIGS. 12-14 depict the digitized anatomical landmarks placed on the image for the purpose of making linear measurements in the front and side views of the subject. Where a three-dimensional image is displayed, the image could be rotated and pan and zoomed to provide the front and side views as well as 'bird's eye' of the subject as well as other views as desired as seen in FIGS. 20A-20D described above.

Method 50 in the embodiment includes a step 66 of calculating postural displacements using the determined pixel to distance ratio. The displacements may include, for example, linear displacements and angular displacements. Method 50 may include a step 68 of presenting a postural analysis 27. Postural analysis 27 may display, for example, the calculated linear or angular displacements 30, 34 and any deviation thereof from a normal or proper posture taking into account, for example, the patient's age, sex, height, and weight. The normal or proper posture itself can be displayed over the displayed patient's image to provide a visual comparison.

Requirements of the mobile, hand-held communication device, the software, and the interaction therebetween, and specific operations or steps of the program for achieving the described functions of the method for an example embodiment are set forth below.

Leveling
Orientation Tracking

Requires an environment that can provide real-time or near real-time horizontal and vertical orientation readings. These readings may be provided by an "accelerometer".

1. Begin reading the orientation data from the accelerometer.
2. Track each reading in a historical array of readings; do not discard old readings.
3. When more than one reading has been tracked, apply a low-pass filter against the newest and the historical readings. This will provide accelerometer readings that more accurately reflect the constant effects of gravity and reduce the influence of sudden motion to the accelerometer.

Head-Up Display (HUD) Overlay

Requires a camera and a display screen that renders the camera's current view. Requires an application programming interface that allows drawing and displaying images over the camera view on the display screen, partially obscuring portions of the camera view. Finally, requires a pre-drawn graphic image files. The graphic image file may be partially transparent with one or more simple horizontal and vertical lines drawn on the image. The image file may also be more complex with circles, swirls, targets, multiple horizontal and vertical lines, etc. The image file will be used twice: once as stationary reference, once as dynamically moving indicator. While only one image is required the visual design may be more appealing using two image files, one for each usage.

1. Initialize the camera and viewpoint through normal methods of those devices.
2. Using the programming interface and apply the image to the display screen.
3. Using the programming interface, adjust the image location so the image is viewable on the display screen. The camera display screen should render both the camera's current view and the image file. This image application will not be modified further and serves the purpose of a stationary reference.
4. Using the programming interface and apply the image to the display screen, again.
5. Using the programming interface, adjust the image location in the exact same manner as the stationary image.
6. Using the programming interface, instruct the display to draw the second image over the first stationary image.
7. The camera display screen should render the camera's current view with both the image files drawn over the camera view, partially obstructing the camera view.
8. The second image's location will be modified later and serves the purpose of a movement indicator.

User Feedback—Leveling the Camera

Requires both the Orientation Tracking and the HUD Overlay methods described above. Orientation readings may be assigned x, y, and z planes which are discussed here as "roll", "pitch", and "yaw".

1. Using the "roll" reading from the accelerometer, apply a rotation to the movement indicator image of the HUD. The programming interface of the display screen overlay will dictate the angle units (i.e. radians, degrees) required to rotate the movement indicator image. Use common angle mathematics to convert the reading to radians or degrees as required.
2. Use the programming interface to apply a standard mathematic rotation matrix to the movement indicator image's coordinate system.
3. The movement indicator image should render partially rotated on the camera display screen.
4. Using the programming interface or the operating system documentation, determine the screen coordinates for the camera display (for example, the iPhone 4S device boasts 960×640 pixel display, however the iOS operating system assigns the size of 320×460; interest here is in the operating system size of 320×460; the operating system will handle conversion between the device display 'space' and the operating system 'space').
5. Using the programming interface or the accelerometer documentation, determine the minimum and maximum values of the accelerometer "pitch" readings (for example, the iOS operating system provides "pitch" readings as fractional decimal in the range of −1.00 through +1.00).
6. Using the programming interface, read the current location coordinate of the center of the movement indicator image.
7. Add or subtract the pitch reading to the vertical location coordinate, restricting the value to the maximum and minimum boundaries of the screen coordinates.
8. Using the programming interface, apply the result of the addition (subtraction) to the movement indicator image.
9. The movement indicator image should be rendered on the camera display screen in a different location. The image's center point should remain within the viewable area of the display screen.
10. The software should continuously monitor the readings of the accelerometer. With each new reading, update the rotation and location coordinates of the movement indicator image as shown above.
11. With one image stationary and a complimentary image moving, the user will be able to visually notice when the image perfectly overlap one another in both location and rotation. This registration is their feedback that the device is oriented correctly.

Display and Physical Measurements

Cropping

Requires a software environment that provides visual display elements (views) that can be nested inside of one another; allowing one element to surround or envelope another. For example, the iOS operating system provides the UIView element (including UIView derivatives). For real-time cropping, requires a display screen that renders the views and any changes to the views (including size, scale, rotation, color, brightness, etc)

1. Create two views, nested inside one another.
2. Load an image into the software (from a camera, disk drive, computer memory, etc)
3. Using the programming interface to assign the image to the inner view.
4. Optionally, use the programming interface to scale the inner view to be larger than the outer view.
5. Optionally, use the programming interface to adjust the location of the views so the inner view's boundaries extend past the outer view equally in all directions.
6. Regardless of completing step 4 and 5, allow the user to manipulate the inner view's size, scale, and location while keeping the outer view fixed in both size, scale, and location. Manipulation may occur by tracking the user input through any computer input device. For example, on the iOS operating system manipulation could be tracked by custom touch-screen readings or standard pinch-and-zoom features.
7. After user manipulation has completed (indicated by an arbitrary user action or input; for example pressing a "Done" button) use the programming interface to read the current size and position of both the inner and outer views.
8. Use the programming interface to capture the portion of the inner view image that is currently within the outer view's boundaries. Any portion of the inner view that extends past the outer view's boundaries will be cropped and discarded.

9. The programming interface may require the cropping boundary to be pre-calculated. The cropping boundary is used by the programming interface and applied to the original image to produce a new image from a portion of the original. The cropping boundary can be calculated with simple arithmetic:
   calculate (or read from the programming interface) the final offset distance between the inner view and outer view's center points,
   calculate (or read from the programming interface) the final resizing scale applied to the inner view,
   use the offset divided by the scale to determine the origin of the cropping boundary
   use the fixed size of the outer view divided by the scale to determine the dimensions of the cropping boundary
   For example, the X coordinate of a cropping boundary calculated in the iOS operating system would be: x=outerview.contentOffset.x/outerview.zoomScale; and the width of the cropping boundary would be: width=outerview.frame.width/outerview.zoomScale;

As an example of calculating the cropping boundary, assume the following:
An image of size 460×460
An outer view of size 300×400
The user has manipulated the inner image view to move it an arbitrary direction and scaled to be twice as large. The result of the manipulation is an image with effective size of 920×920 (×2 scale) with an offset of 195 in the X coordinate direction and 289 in the Y coordinate.
The X coordinate of the cropping box would be 195/2=97.5 and the width of the cropping box would be 300/2=150.
For reference, the Y coordinate in this example would be 144.5 and the height 200.
The programming interface should produce a new image from the region of the original image with top left corner at 97.5, 144.5, width of 150 and height of 200.

Pixel Distance

Requires an image of an object cropped in a manner that the top and bottom of the object are at the edges of the top and bottom of the image, and the physical height of the object must be known. Requires a software environment that can interpret image data and provide pixel dimensions of the image.
1. Load the image into the software (from a camera, disk drive, computer memory, etc)
2. Use the programming interface to read the pixel height of the image
3. Divide the known height of the object by the pixel height reading to determine the ratio of pixels to physical distance
4. The ratio can be used to calculate and convert any distance of pixels to physical distances by multiplying the ratio and the pixel distance For example, given an image that is 1000 pixels in height and an object that is known to be 60 inches in height we can calculate:
Each pixel represents 0.06 physical inches: 60/1000=0.06
A distance of 250 pixels represents 15 physical inches: 0.06×250=15

Figure 11:
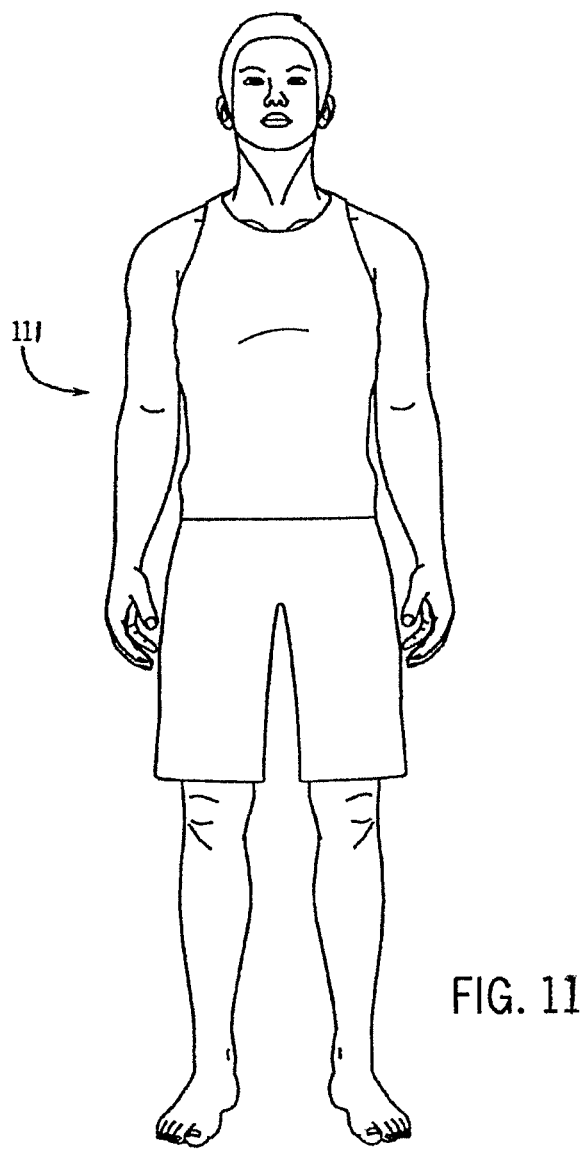
FIG. 11 is a front view of a subject for which an exemplary embodiment of the invention may make measurements either for postural screening as explained with reference to FIGS. 1-10 or for measuring the dimensions of the human body in the other embodiments as disclosed herein.

Referring to FIG. 11, a subject 111 is illustrated whose measurements may be taken by an exemplary embodiment of the invention.

Referring to FIG. 12 and FIG. 13 an exemplary embodiment of the invention is illustrated where the subject of FIG. 11 is displayed on the display screen 13 of a mobile digital device 12. Anatomical landmarks 116 digitized by the user's touching the screen at the anatomical landmarks thereon are highlighted on the side view of the subject in FIG. 13. As pertains to FIG. 12, the anatomical landmarks 116 are illustrated on a front view of the subject.

Figure 15:
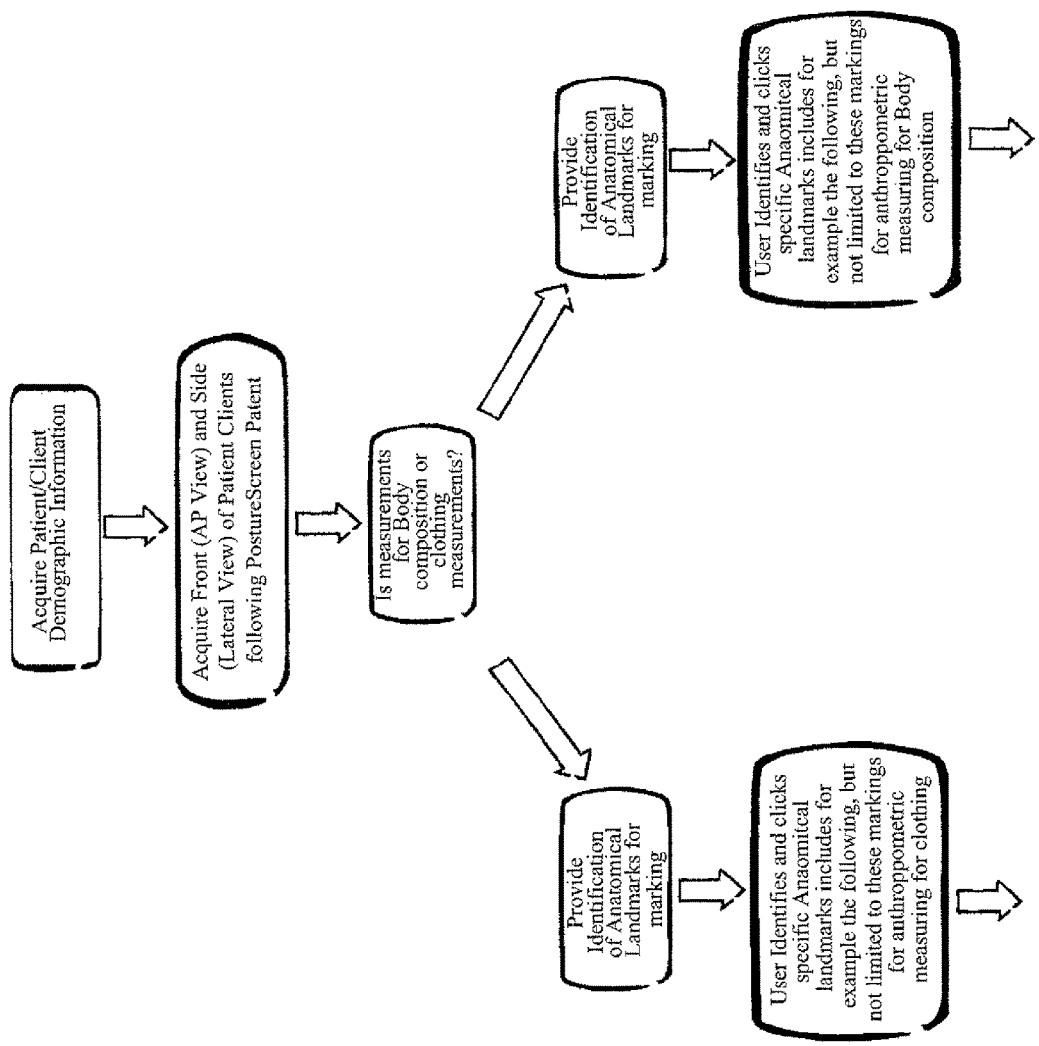
FIG. 15 is a flow chart of operations possible with the mobile device of an embodiment of the invention affording measurements for body composition or clothing measurements.
Figure 16:
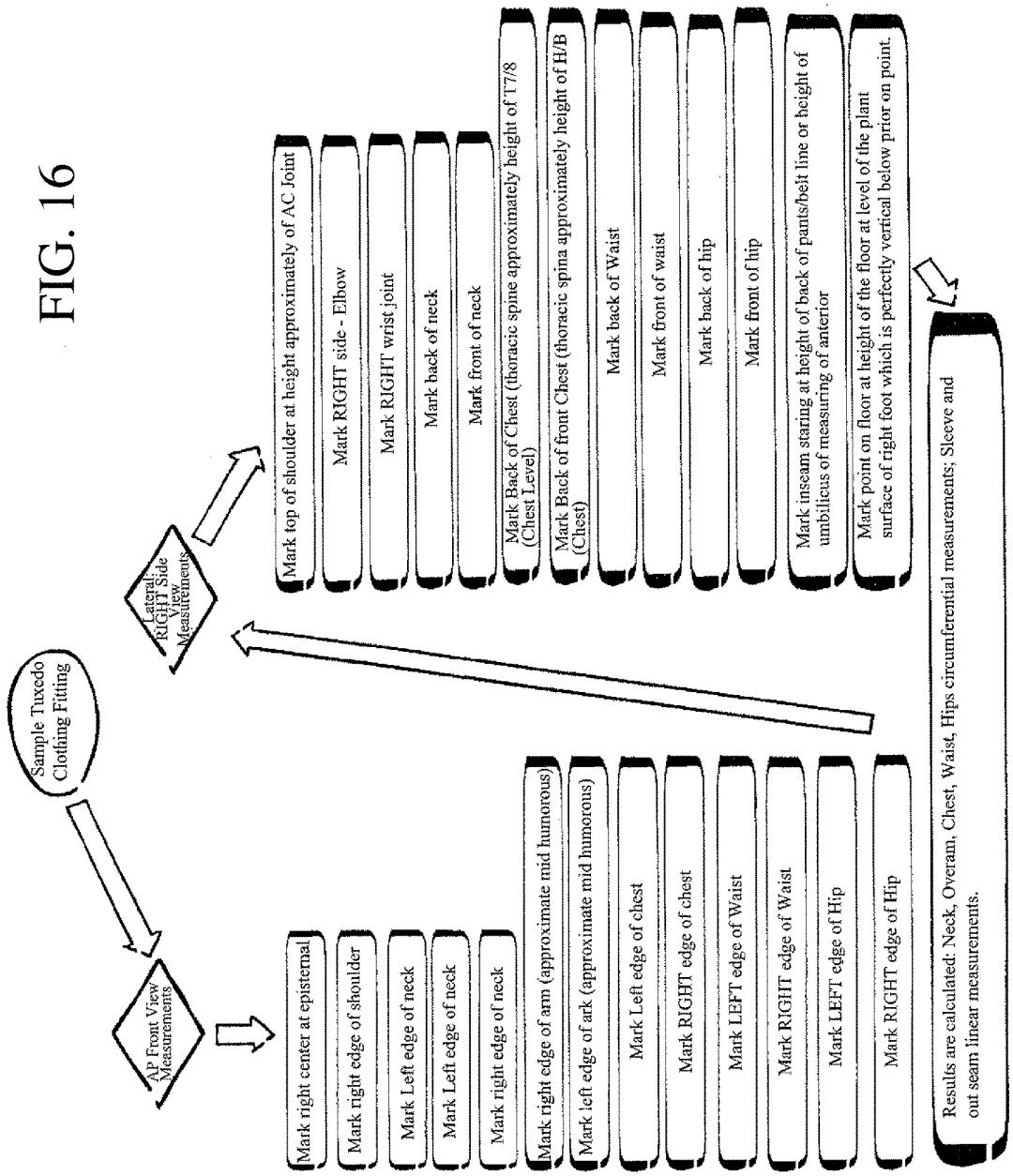
FIG. 16 is a flow chart of steps for obtaining measurements for clothing, particularly tuxedo/suit fitting, in accordance with the invention.
Figure 18:
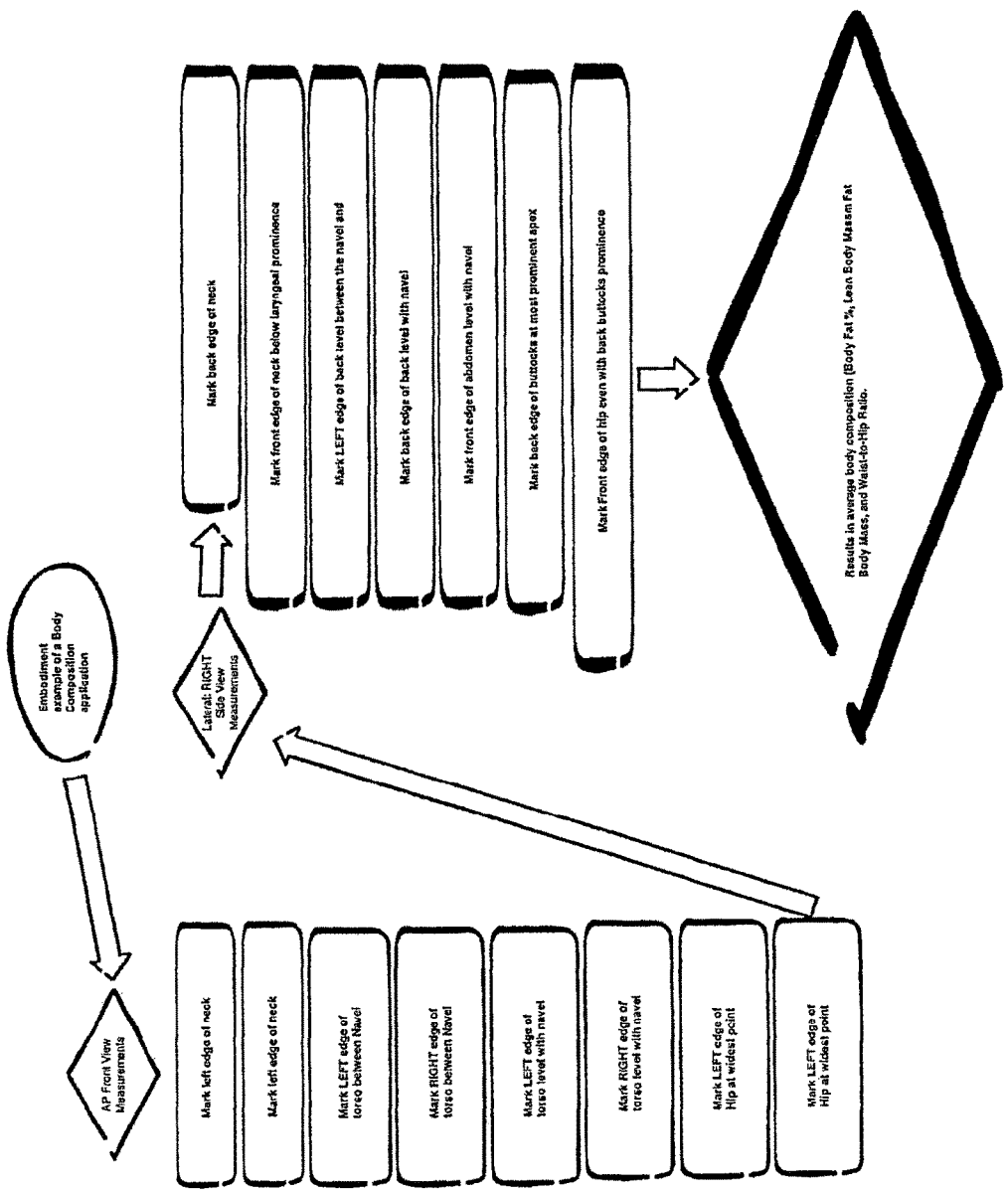
FIG. 18 is a flow chart of steps for obtaining measurements for estimating body composition using the mobile device of the invention for making measurements in accordance with the invention.
Figure 20B:
FIGS. 20A-20D are three-dimensional analysis examples of posture analysis (torso) using a mobile communication device with 3D scanner/camera wherein the end user can pan and zoom and rotate to analyze the subject in any plane.
Figure 20A:
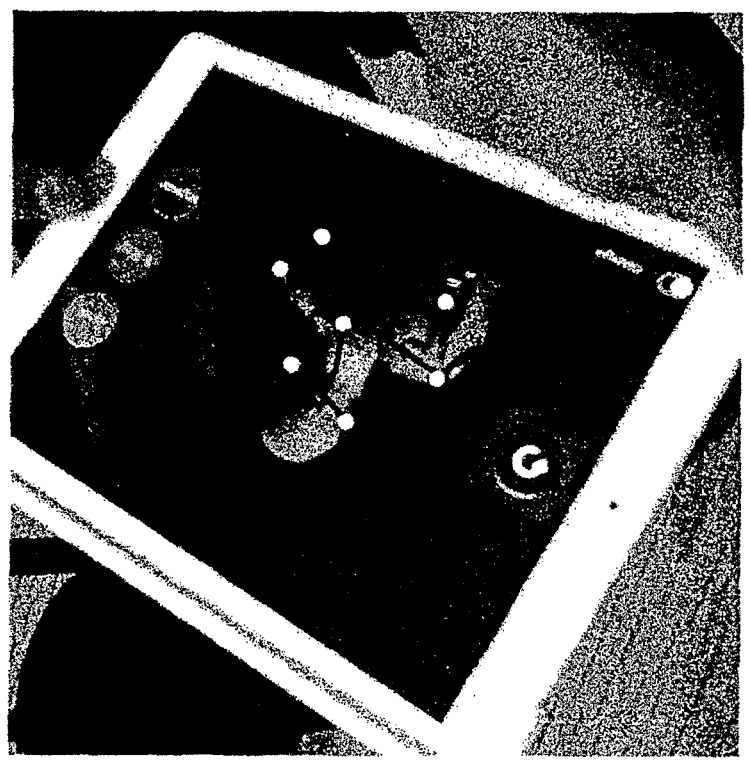
Figure 20D:
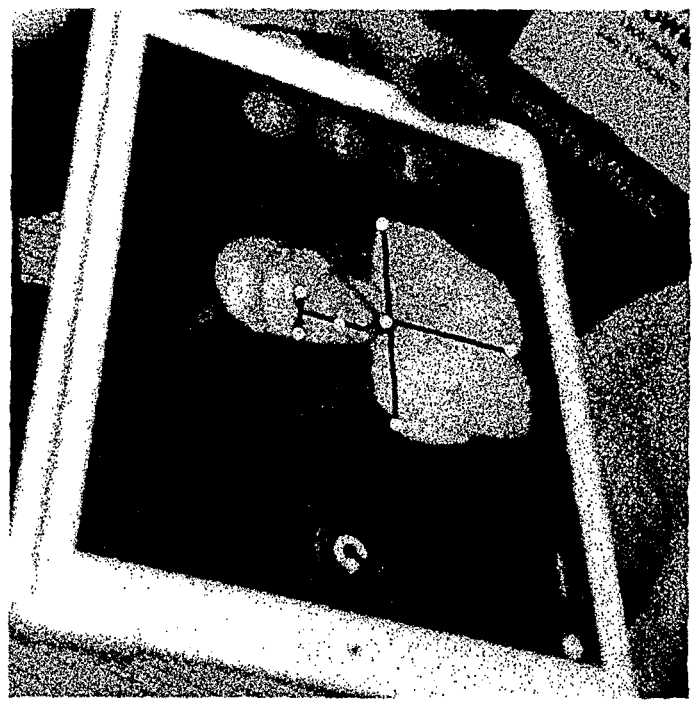
Figure 20C:
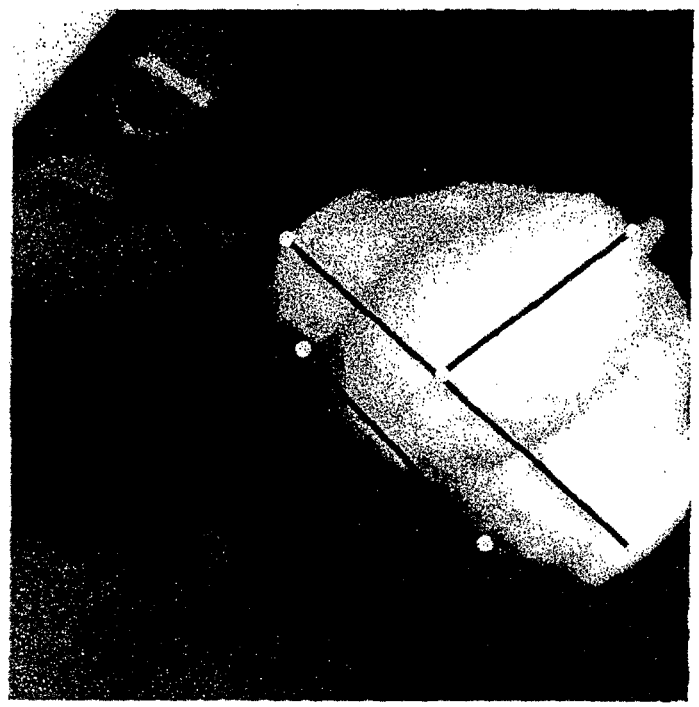

Referring to FIG. 14, anatomical landmarks 116 are illustrated on the subject in an exemplary embodiment of the invention. FIG. 14 also illustrates the measured distance from shoulder to elbow 118; the measured distance from elbow to hand 200; the measured distance from front to back of chest 220 and the measured distance from front to back of waist 240. The flow charts of the steps for the methods are shown in FIGS. 15, 16 and 18. Images with digitized anatomical landmarks used in the methods are shown on the displayed images in FIGS. 17 and 19.

In the clothing measurement of FIGS. 16 and 17, the embodiment is a clothing fitting. In this case, the measurements are those needed for a suit or tuxedo. The measurements shown in the drawings are made or calculated from linear measurements as shown. The circumferential calculations for neck, waist, hip and chest are made as described below for circumferential calculations from linear measurements. Additionally, the shirt sleeve length and outseam measurements are made as shown in FIG. 17.

In the body composition example of FIGS. 18 and 19, the application embodiment can be applied to measurements needed for body composition analysis which includes circumferential measurements (traditionally performed with a tape measure) for assessment of percentage body fat. Additionally one can calculate waist to hip ratio which is also a circumferential measurement. These are important health related diagnostic assessments with regards to body morphology and type.

Examples of known mathematical formulae useful in the several embodiments include a body circumference formula employed in the example embodiments which utilizes measured body width (measured distance from left to right edges of body) and measured body depth (distance from back to front edges of body) made in front view and side view images of the body, respectively.

The circumferential estimation is taken as the average of the results of both the equations (1) and (2) below. These are known formulas by a mathematician and his formulae, referred to as the "Ramanujan's formula". The circumference of the ellipse with half axes a and b half of the distance from each of the body width and body depth measurements is given below where the approximation is from Ramanujan's formula:

$$C \approx \pi\left[3(a+b) - \sqrt{(3a+b)(a+3b)}\right] = \pi\left[3(a+b) - \sqrt{10ab + 3(a^2 + b^2)}\right]$$ Equation (1)

and $$C \approx \pi(a+b)\left(1 + \frac{3\left(\frac{a-b}{a+b}\right)^2}{10 + \sqrt{4 - 3\left(\frac{a-b}{a+b}\right)^2}}\right).$$ Equation (2)

If a=b then the ellipse is a circle with radius r=a=b and these formulas give you C=2*pi*r.

Body composition in terms of body fat is calculated using the steps and measurements indentified in FIGS. 17-19 then calculating circumference for neck, waist, abdomen and hip and obtaining the height and then through data entry in one of the known formulae as set forth below where all circumference and height measurements are in inches.

Males.

% body fat=86.010×log 10(abdomen−neck)−70.041× log 10(height)+36.76

Females.

% body fat=163.205×log 10(waist+hip−neck)− 97.684×log 10(height)−78.387

Other known formulae describing known morphological relationships for body fat could be employed as will be understood by the skilled artisan. For example, the results from several known formulae could be averaged.

Examples of known formulae are presented in the publications listed below, which are incorporated herein by reference:

Hodgdon, J. A. and M. B. Beckett (1984) *Prediction of percent body fat for U.S. Navy men from body circumferences and height*. Report no. 84-11, Naval Health Research Center, San Diego, Calif.;

Hodgdon, J. A. *Body* (1990) *Composition in the Military Services: Standards & Methods*. Report No. 90-21 Naval Health Research Center, San Diego, Calif.;

It should be understood, of course, that the foregoing relates to exemplary embodiments of the invention and that modifications may be made without departing from the spirit and scope of the invention as set forth in the following claims. For example, clothing measurements are not limited to tuxedo or suit measurements but could be made for other clothing items, e.g. dresses, shirts, blouses, etc. Body composition is also not limited to body fat but can include other estimations such as for body mass index, waist-to-hip ratio, lean body mass, etc, using known morphological relationships. A three-dimensional image of the patient's foot can also be used according to the disclosed method for making measurements for making custom fit orthotics and inserts as will be readily understood by the skilled artisan. Likewise, the anatomical predictions can include other predictions than those in the specific embodiments described herein without departing from the scope of the invention as recited in the appended claims. Likewise, the digital display screen need not be a touch screen display as in the example embodiments but otherwise allowing, as by clicking a mouse, for example, to demark various anatomical landmarks thereon in accordance with the invention, as will be readily understood by the person skilled in the art.

The invention claimed is:

1. A method of deriving an anatomical prediction using a known morphological relationship and a programmed apparatus including a digital touch screen display and a 3D camera configured to acquire an image of a person on the digital touch screen display, the method comprising:
    acquiring at least one digital three-dimensional image of a person on the digital touch screen display;
    digitizing points on a plurality of anatomical landmarks on the displayed three-dimensional image;
    calculating a circumferential measurement of at least a portion of a body of a person in the displayed three-dimensional image using at least the digitized points on the displayed three-dimensional image; and
    making an anatomical prediction based on the calculated circumferential measurement and a known morphological relationship.

2. The method of claim 1, wherein the anatomical prediction is a clothing measurement.

3. The method of claim 2, wherein the clothing measurement is selected from the group consisting of neck, overarm, chest, waist, hips, sleeve and outseam.

4. The method of claim 1, wherein the anatomical prediction is a body composition.

5. The method of claim 1, further comprising activating the 3D camera to acquire the three-dimensional image of the person,
    wherein the programmed apparatus is a mobile, hand-held communication device having the 3D camera.

6. The method of claim 1, wherein the anatomical prediction is a volume of a body part.

7. The method of claim 1, wherein the points on the plurality of anatomical landmarks are digitized by touching the digital touch screen display of the image at respective anatomical landmarks.

8. The method of claim 1, wherein the digital three-dimensional image is a foot of the person and the method further comprises using the anatomical prediction for orthotic or insert manufacturing.

9. The method of claim 1, wherein the circumferential measurement of the at least the portion of the body of the person in the displayed three-dimensional image is calculated by adding a linear distance between the digitized points on the displayed three-dimensional image along a predetermined two-dimensional plane of the image.

10. The method of claim 1, including displaying the anatomical prediction on the digital touch screen display.

11. The method of claim 1, wherein the anatomical prediction is a postural displacement.

12. A method for making an anatomical measurement of a body of a person, the method comprising:
    providing a digital anthropometer on a mobile device;
    acquiring at least one digital three-dimensional image of a body of a person and displaying the digital three-dimensional image on the device; and
    digitizing anatomical landmarks provided on the digital three-dimensional image displayed on the device for calculating a circumferential measurement of the body of the person.

13. A system for determining an anatomical measurement of a body of a person, the system comprising:
    a programmed device comprising a digital touch screen display having an array of pixels;
    a 3D camera configured to acquire a three-dimensional image of a at least a portion of a body of a person on the digital touch screen display,
    a digital anthropometer configured to digitize anatomical landmarks on the three-dimensional image of the at least the portion of the body of the person displayed on the digital touch screen display in order to calculate a circumferential measurement of the at least the portion of the body of the person; and
    a controller configured to make an anatomical prediction using the circumferential measurement and a known morphological relationship.

14. The system according to claim 13, wherein the anatomical prediction is a clothing measurement.

15. The system according to claim 13, wherein the anatomical prediction is a body composition.

16. The system according to claim 13, wherein the anatomical prediction is a postural displacement.

17. The system according to claim 13, wherein the anatomical prediction is configured for use in orthotic or insert manufacturing.

18. The system according to claim 13, wherein the programmed device is a mobile, hand-held communication device.

\* \* \* \* \*